(12) United States Patent
Koshijima et al.

(10) Patent No.: US 11,191,676 B2
(45) Date of Patent: Dec. 7, 2021

(54) DEVICE AND METHOD FOR PRODUCING STRETCHABLE LAMINATE FOR WEARABLE ARTICLE

(71) Applicant: ZUIKO CORPORATION, Osaka (JP)

(72) Inventors: Miwa Koshijima, Osaka (JP); Hideyuki Nakamura, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 57 days.

(21) Appl. No.: 16/614,736

(22) PCT Filed: Jun. 13, 2018

(86) PCT No.: PCT/JP2018/022518
§ 371 (c)(1),
(2) Date: Nov. 18, 2019

(87) PCT Pub. No.: WO2019/003908
PCT Pub. Date: Jan. 3, 2019

(65) Prior Publication Data
US 2020/0179180 A1   Jun. 11, 2020

(30) Foreign Application Priority Data

Jun. 29, 2017  (JP) .............................. JP2017-127603

(51) Int. Cl.
*A61F 13/15* (2006.01)
*B32B 5/02* (2006.01)
*B32B 37/10* (2006.01)

(52) U.S. Cl.
CPC .. *A61F 13/15731* (2013.01); *A61F 13/15764* (2013.01); *B32B 5/022* (2013.01);
(Continued)

(58) Field of Classification Search
CPC ..... B32B 2307/51; B32B 5/022; B32B 37/10; B32B 2555/02; A61F 13/15739;
(Continued)

(56) References Cited

U.S. PATENT DOCUMENTS

2006/0270302 A1* 11/2006 Ando .................. A61F 13/4902
442/328
2018/0147095 A1   5/2018 Koshijima et al.

FOREIGN PATENT DOCUMENTS

EP        3527182 A1    8/2019
JP     2005-212405 A    8/2005
(Continued)

OTHER PUBLICATIONS

International Search Report Issued in PCT/JP2018/022518 dated Aug. 7, 2018.

*Primary Examiner* — Vishal I Patel
(74) *Attorney, Agent, or Firm* — Renner, Otto, Boisselle & Sklar LLP (57) ABSTRACT

There are disposed, in a width direction of an anvil roll, a plurality of first projections for producing joint portions where a pair of sheets are jointed to each other; each of the first projections extends in a circumferential direction of the anvil roll and includes a carrying groove carrying an elastic member while the elastic member has entered in the groove; and between one first projection and another first projection adjacent to each other in the width direction, at least one receiving part for receiving the pair of sheets is arranged.

7 Claims, 10 Drawing Sheets

(52) U.S. Cl.
    CPC .......... *B32B 37/10* (2013.01); *B32B 2307/51* (2013.01); *B32B 2555/02* (2013.01)

(58) Field of Classification Search
    CPC ............ A61F 13/15731; A61F 13/4902; A61F 13/15593; A61F 13/15764; B29C 66/83511; B29C 66/7294; B29C 66/73921; B29C 66/21; B29C 66/1122; B29C 66/81433; B29C 66/433; B29C 65/086; B29K 2995/0046; B29L 2031/4878
    See application file for complete search history.

(56) References Cited

FOREIGN PATENT DOCUMENTS

| | | | |
|---|---|---|---|
| JP | 5256114 B2 | 8/2013 | |
| JP | 2016-78363 A | 5/2016 | |
| WO | WO 2016/208502 A1 | 12/2016 | |
| WO | WO-2016208513 A1 * | 12/2016 | ......... A61F 13/4902 |

* cited by examiner

DEVICE AND METHOD FOR PRODUCING STRETCHABLE LAMINATE FOR WEARABLE ARTICLE

TECHNICAL FIELD

The prevent invention relates to production of a stretchable laminate for a wearable article.

BACKGROUND ART

In the following prior art, the stretchable laminate is formed by disposing a plurality of elastic members between two sheets and jointing the two sheets to each other intermittently in both directions of the stretching direction of the elastic members and the direction crossing the stretching direction.

CITATION LIST

Patent Literature

First patent document: JP2005-212405A (front page)

SUMMARY OF INVENTION

Both sheets are jointed by passing between an anvil roll having projections and a sonic horn or the like (heating/pressurizing means) facing the anvil roll. To reduce a pressure at the time of jointing, the elastic members are housed in carrying grooves provided on the projections.

The above-described projection for jointing is formed to have a height of 100 μm or larger, for example, so as to house the stretched elastic member in the carrying groove.

However, the sheets wound on the anvil roll tend to shrink in the radial direction of the anvil roll due to carrying tension, and may unexpectedly displace in the axial direction of the anvil roll. If the displacement of the sheets causes displacement of the elastic member as well, the elastic member may be removed from the carrying groove and ruptured by pressing force at the time of jointing.

The present invention aims at providing a method and device for producing a stretchable laminate for a wearable article while suppressing removal of the elastic member from the carrying groove and rupture of the elastic member, when the both sheets are jointed to each other on the anvil roll with projections provided intermittently in the axis direction.

The present invention includes an anvil roll 50 that carries a pair of first and second sheets 1, 2 and elastic members F so that the elastic members F are sandwiched between the pair of first and second sheets 1, 2, and a fusion device 70 that, in cooperation with the anvil roll 50, fuses the pair of first and second sheets 1, 2 mutually and makes the pair of first and second sheets 1, 2 hold the elastic members F, wherein an outer peripheral surface 51 of the anvil roll 50 includes a plurality of first projections 52H for producing first joint portions 31 where the pair of first and second sheets 1, 2 is jointed to each other, the first projections being provided along a width direction S of the anvil roll 50 and spaced from each other in the width direction S, each of the first projections 52H defines and includes a carrying groove G extending in a circumferential direction R of the anvil roll 50 and carrying each of the elastic members F while each of the elastic members F has entered (been housed) in the groove G, and at least one receiving part 52L for receiving the pair of first and second sheets 1, 2 is arranged (disposed) between one first projection 52H and another first projection 52H adjacent to each other in the width direction S, among the plurality of first projections 52H each including the carrying groove G.

In a method for producing a stretchable laminate according to the present invention, the stretchable laminate 10 including the elastic members F spaced from each other and sandwiched by the pair of first and second sheets 1, 2, the pair of first and second sheets 1, 2 being jointed to each other at each of the first joint portions 31, the first joint portions arranged in columns in a stretching direction Df of the elastic members F and arranged in rows in a direction Dp crossing the stretching direction Df, the method includes the following steps. That is, the present method includes:

a step of introducing the first sheet 1 of the pair of first and second sheets onto the anvil roll 50;

a step of introducing the elastic members F onto the first sheet 1 on the anvil roll 50 and introducing the elastic members F so that each of the elastic members F enters (are housed) in each of the carrying grooves G of the anvil roll 50;

a step of carrying the first sheet 1 and the elastic members F while receiving the first sheet 1 at the at least; one receiving part 52L between the one first projection 52H and the another first projection 52H, each including the respective carrying grooves G, so as to suppress shrinkage of the first sheet 1 in a radial direction of the anvil roll 50;

a step of introducing, on the anvil roll 50, the second sheet 2 of the pair of first and second sheets, onto the first sheet 1 so as to sandwich the elastic members F between the first sheet 1 and the second sheet 2; and a step of forming the first joint portions 31 by fusing the first sheet 1 and the second sheet 2 on the one and the another first projections 52H of the anvil roll 50 without fusing the first sheet 1 and the second sheet 2 at the receiving part 52L.

In the present invention, the carrying groove G included in the first projection 52H is provided so that at least one carrying groove G for one first projection 52H divides a projection surface of the one first projection 52H in the width direction S. That is, each of the carrying grooves G is a V-shaped or U-shaped notch, for example, and is defined by a surface of the notch formed in the first projection 52H in the center in the width direction S of the first projection 52H.

The depth of the carrying groove G may be a depth with which the pair of sheets 1, 2 and the elastic member F therebetween are fused mutually or a depth with which they are not fused mutually. In the case where the pair of sheets 1, 2 and the elastic member F are fused mutually in the carrying groove G, a bottom surface of the carrying groove G is defined by the first projection 52H. That is, in such a case, the carrying groove G is surrounded by the first projections 52H on both sides in the width direction S and the lower side.

Note that a plurality of carrying grooves G may be provided for one first projection 52H.

In the present invention, a pair of sheets are jointed to each other by a fusing structure at least at; a pair of joint portions on both sides in the width direction (the crossing direction) of each of the elastic members. That is, the pair of sheets are jointed to each other by the fusing structure at least at a pair of first projections 52H on both sides of each carrying groove G, so as to generate a stretchable laminate in which the elastic member F is sandwiched between the pair of sheets.

On the anvil roll, the sheet is received by the receiving part between the projections for jointing. As such, this suppresses displacement of the sheets and the elastic members F in the axis direction (width direction) of the anvil roll. As a result, this is expected to suppress the removal of the elastic members from the carrying grooves and the rupture of the elastic members at the time of jointing.

BRIEF DESCRIPTION OF DRAWINGS

FIG. 3 illustrates a region of a nonwoven fabric sheet in grey. FIG. 2A illustrates joint portions with oblique lines. FIG. 8A illustrates projection surfaces of the first and second projections with oblique

DESCRIPTION OF EMBODIMENTS

In the preferred device, the receiving part comprises at least two receiving parts 52L provided between the one first projection 52H and the another first projection 52H, and a second projection 52S for producing a second joint portion 32 where the pair of first and second sheets 1, 2 is jointed to each other is provided between the at least two receiving parts 52L.

The height of the receiving part 52L is preferably smaller by 51 to 300 μm than the height of the first projection 52H.

If the height of the receiving part 52L is excessively smaller than that of the first; projection 52H, the first sheet tends to shrink in the radial direction of the anvil roll 50 together with the elastic member F before the first sheet is received by the receiving part 52L, thus causing the elastic member F to easily displace in the axis direction of the anvil roll 50.

On the other hand, if the height of the receiving part 52L is close to the same degree of the first projection 52H, the pair of sheets easily fuse mutually to be disadvantageously jointed to each other at the receiving part 52L, depending on the thickness and the kind of the sheets.

From such a viewpoint, the height of the receiving part 52L is preferably smaller by 60 to 300 μm than that of the first projection 52H, more preferably smaller by 70 to 300 μm, still more preferably smaller by 70 to 250 μm, and most preferably smaller by 70 to 200 μm.

However, depending on the kind and thickness of the sheets, a difference of the height may be around 20 to 300 μm.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

EXAMPLE

Prior to the description of an example of the stretchable laminate, there is described an example of a structure of a disposable wearable article in which the stretchable laminate is used.

Figure 1:
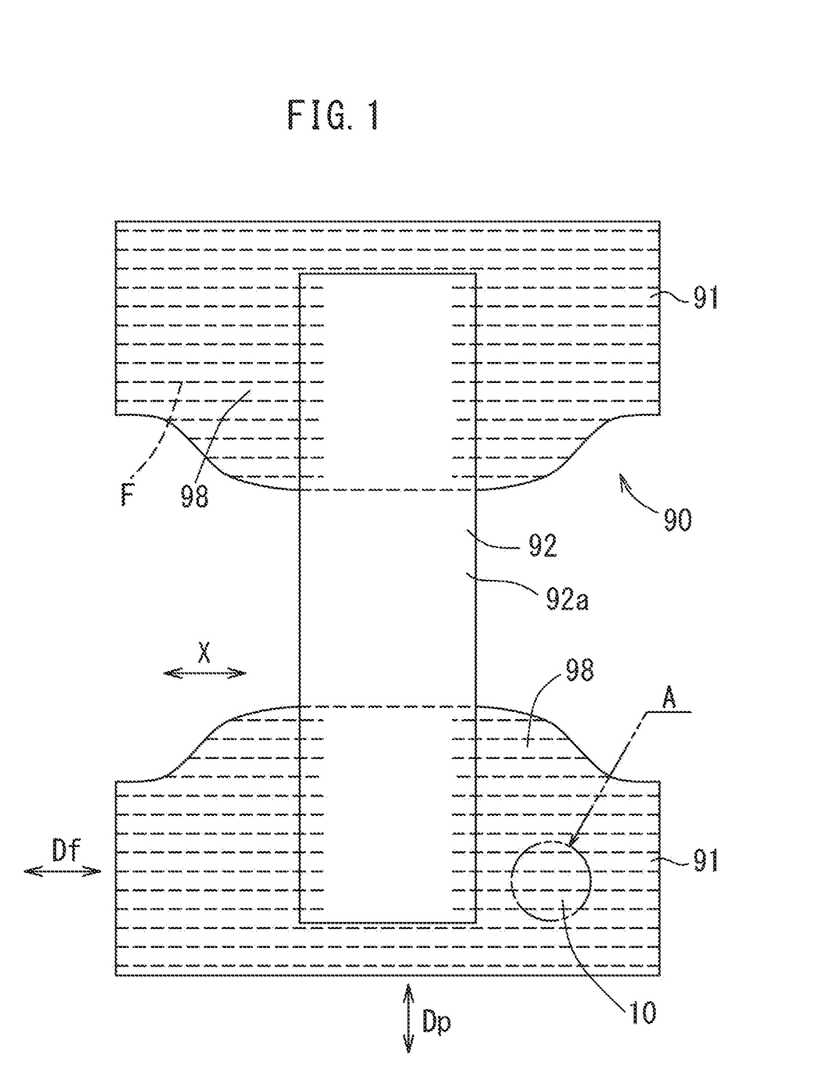
FIG. 1 is a plane view illustrating an example of an expanded wearable article to which the present; invention is applied.

In FIG. 1 illustrating an expanded wearable article, a wearable article 90 includes an absorbent body 92, and a pair of front and rear around-torso members 91, 91. The absorbent body 92 is extended between the pair of around-torso members 91, 91 to form a crotch part 92a.

The wearable article 90 is worn in the state where the crotch part 92a is folded in half along a virtual line parallel to the around-torso direction X. In this manner, ends in the around-torso direction X of the around-torso members 91, 91 overlap each other.

Figure 2A:
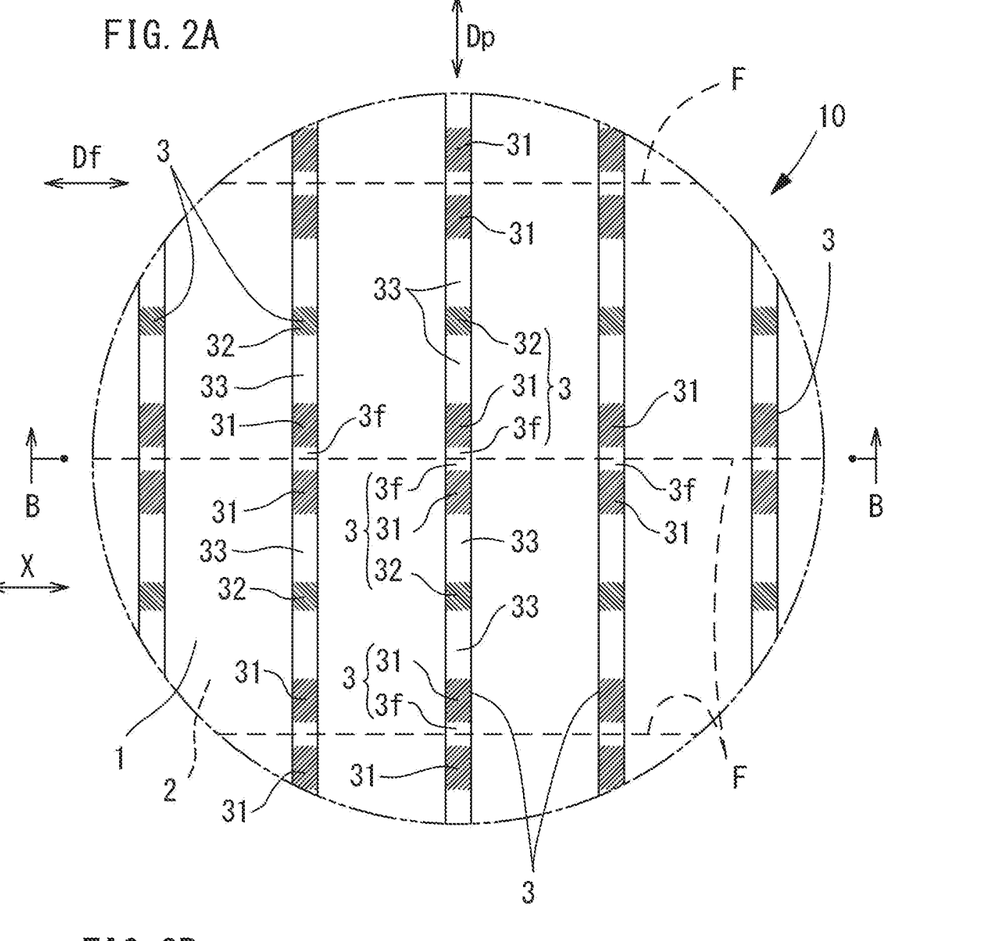
FIG. 2A is an enlarged plane view of an A part (stretchable laminate) according to a first example.
Figure 2B:
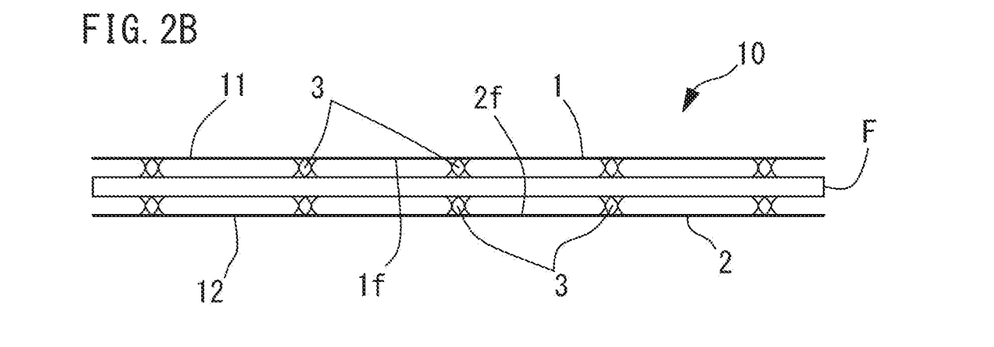
FIG. 2B is an enlarged section view of the stretchable laminate according to the first example.

Each of the front and rear around-torso members 91 includes the stretchable laminate 10 illustrated clearly in FIG. 2A and FIG. 2B. The stretchable laminate 10 is a sheet-form member in which the elastic member F, and the first and second sheets 1, 2 are laminated on one another.

The first sheet 1 and the second sheet 2 are formed of a breathable nonwoven fabric. The elastic member F is sandwiched between the first sheet 1 and the second sheet 2, and is stretchable in the around-torso direction X.

The stretchable laminate 10 of the wearable article 90 (FIG. 1) includes a skin surface 11 (FIG. 2B) to be in contact with the skin of a wearer and a non-skin surface 12 on the opposite side.

The following will describe an example of the stretchable laminate 10.

First, the elastic member F in the stretched state will be described.

As illustrated in FIG. 2B, in the pair of sheets 1, 2, first surfaces 1f, 2f face each other or are in contact with each other. The plurality of elastic members F are disposed between the first surfaces 1f, 2f of the pair of sheets 1, 2, and spaced away from each other, as illustrated by broken lines in FIG. 2A.

As illustrated in FIG. 2A and FIG. 2B, the pair of sheets 1, 2 are jointed to each other at a plurality of joint portions 3 by fusion bonding without an adhesive. In the case of the present example, the pair of sheets 1, 2 are fused to the elastic members F at fixing parts 3f (fusing structure), whereby each of the elastic members F are fixed to the pair of sheets 1, 2 at the fixing parts 3f.

Each of the joint portions 3 is formed by the pair of sheets 1, 2 fused mutually on the first; surfaces 1f, 2f of the pair of sheets 1, 2 in FIG. 2B. The joint portions 3 extend in a direction Dp crossing (e.g., orthogonal to) the stretching direction Df of the elastic member F in FIG. 2A, and are spaced from each other in the stretching direction Df.

In FIG. 2A, each of the joint portions 3 includes a plurality of pairs of first joint portions 31, second joint portions 32, and fixing parts 3f. Between the first joint portion 31 and the second joint portion 32, there is provided a non-joint portion 33 in which the pair of sheets 1, 2 are not jointed to each other.

Figure 3:
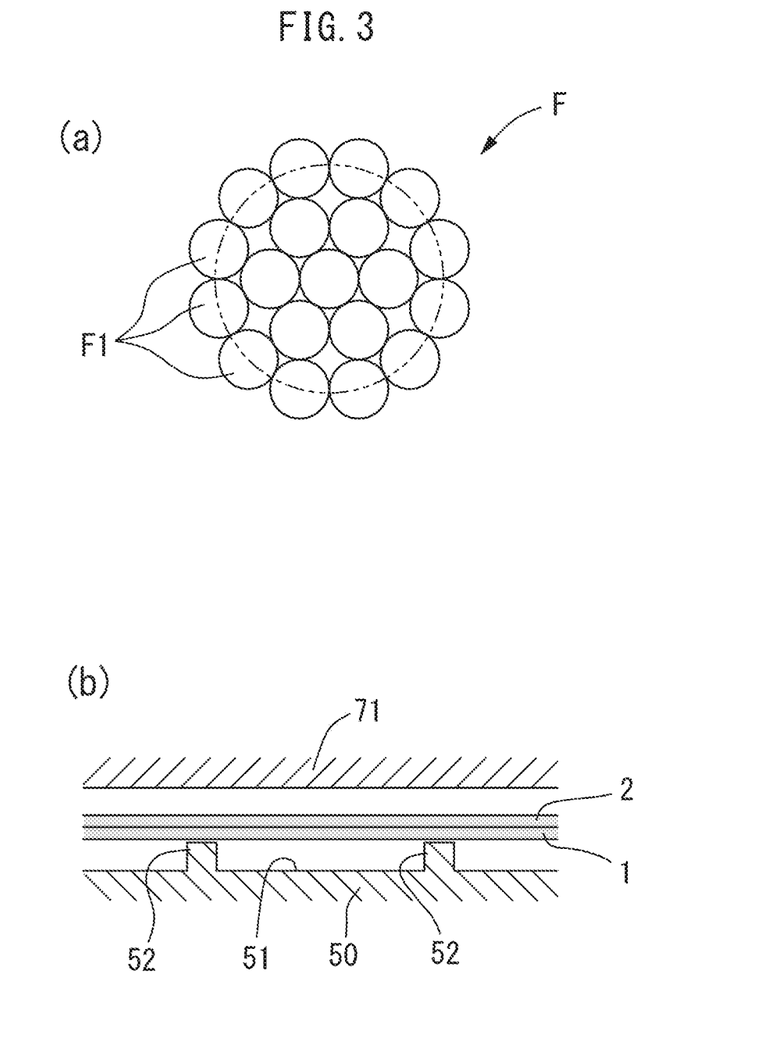
FIG. 3(a) is a section view of an elastic strand.
FIG. 3(b) is a section view of a pair of sheets in a state before fusion.

The elastic member F may be linear or of rope form. For example, as illustrated in FIG. 3(a), the elastic member F may be a multi-strand in which a plurality of rubber threads (fibrous elastic body) F1 are gathered in a bundle. The material of the rubber threads F1 may be polyurethane, for example.

Figure 4A:
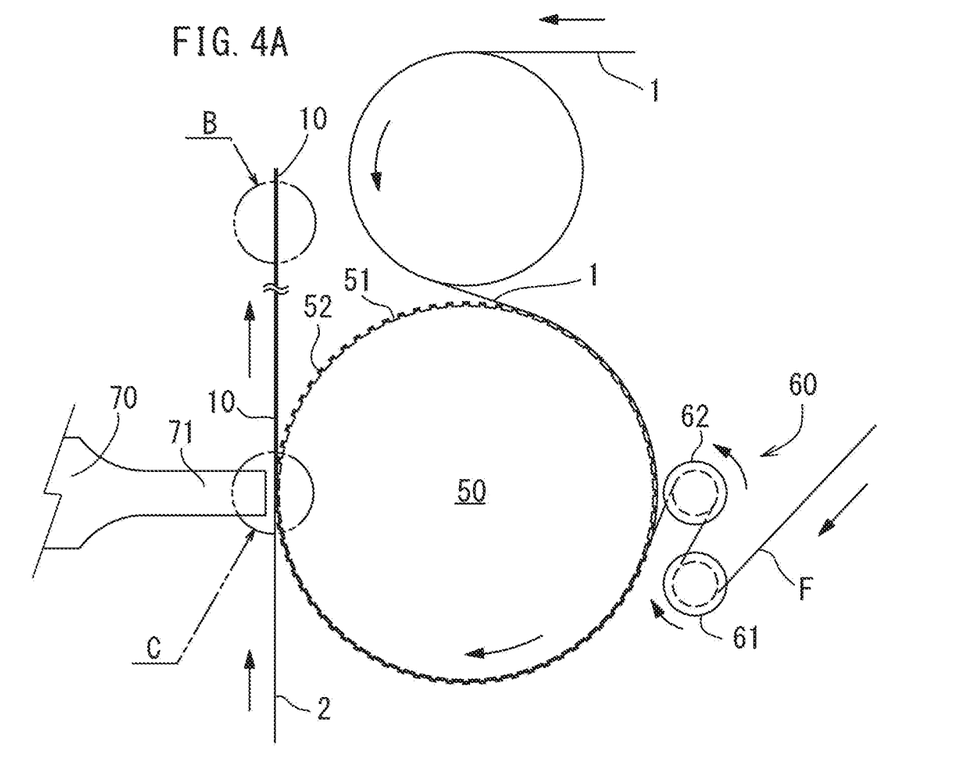
FIG. 4A is a layout diagram illustrating a production device of the present invention.
Figure 4B:
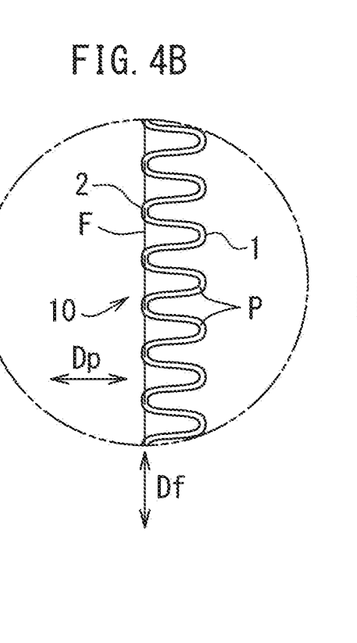
FIG. 4B is a conceptual diagram of an enlarged B part.

In the state where the elastic members F are shrunk, the stretchable laminate 10 forms a number of pleats P by a shrinkage force of the elastic members F, as illustrated in FIG. 4B. The following will describe the stretchable laminate 10 in the state where the elastic members F are shrunk.

The sheets 1, 2 may be thermoplastic nonwoven fabrics in which a number of thermoplastic fibers are laminated. The pleats P of FIG. 4B are formed by the pair of sheets 1, 2 projecting in the direction Dp as in FIG. 4B in the state where the elastic members F of FIG. 2A are shrunk.

FIG. 2A illustrates the first and second joint portions 31, 32 with diagonal lines. The pair of first joint portions 31 are disposed on both sides in the crossing direction Dp of each of the elastic members F.

The second joint portion 32 is disposed between adjacent elastic members F of the elastic members F and between a pair of first joint portions 31 and another pair of first joint portions 31 adjacent to the pair in the crossing direction Dp. In the present example, one second joint portion 32 is provided between a pair of joint portions 31 and another pair of first joint portions 31.

The jointing force of the pair of sheets 1, 2 at the second joint portion 32 may be smaller or larger than the jointing force of the pair of sheets 1, 2 at the first joint portion 31.

In FIG. 2A, the fixing part 3f illustrated by a blank between the pair of first joint portions 31 may have a smaller or larger jointing force than the first joint portion 31. Moreover, the fixing part 3f may have a smaller or larger jointing force than the second joint portion 32. This is because it is sufficient if the elastic member F is fixed to the sheets 1, 2.

At the fixing parts 3f of FIG. 2A, each of the sheets 1, 2 may be fused to the elastic members F, or a part or all of fibers of the nonwoven fabric may be entangled with the elastic members F and fixed thereto.

In the case where the elastic members F are fixed between the pair of sheets 1, 2 of FIG. 2B at both ends of the around-torso members 91, 91 of FIG. 1 or at the vicinity of the both ends, the fixing parts 3f of FIG. 2A are not necessary.

In FIG. 2A, the joint portions 31, 32 are provided intermittently in the crossing direction Dp. Therefore, between the joint portions 31, 32 adjacent to each other, there are provided intermittently the non-joint portions 33 where the first and second sheets 1, 2 are not jointed to each other.

The following will describe an example of the production device of the stretchable laminate 10.

The production device of FIG. 4A includes the anvil roll 50, an introducing device 60, a fusion device 70, and the like.

The introducing device 60 guides and introduces the elastic member F to the anvil roll 50. Moreover, the first sheet 1 is introduced to the anvil roll 50 at a point further upstream than the elastic member F, and the second sheet 2 is introduced to the anvil roll 50 at a point further downstream than the elastic member F. The anvil roll 50 carries the pair of sheets 1, 2 and the elastic member F so that the elastic member F is disposed between the pair of sheets 1, 2.

In cooperation with the anvil roll 50, the fusion device 70 fuses the pair of sheets 1, 2 mutually and fuses the sheets 1, 2 to the elastic member F so that the sheets 1, 2 hold the elastic member F. In the case of the present example, the fusion device 70 is an ultrasonic fusion device performing the fusion bonding by ultrasonic energy.

The fusion device 70 provides vibrational energy at a plurality of joint portions 3 (FIG. 2A) of the two nonwoven fabric sheets 1, 2 in the stretchable laminate 10 of FIG. 2B, so as to fuse the two nonwoven fabric sheets 1, 2 and the elastic member F.

Figure 5:
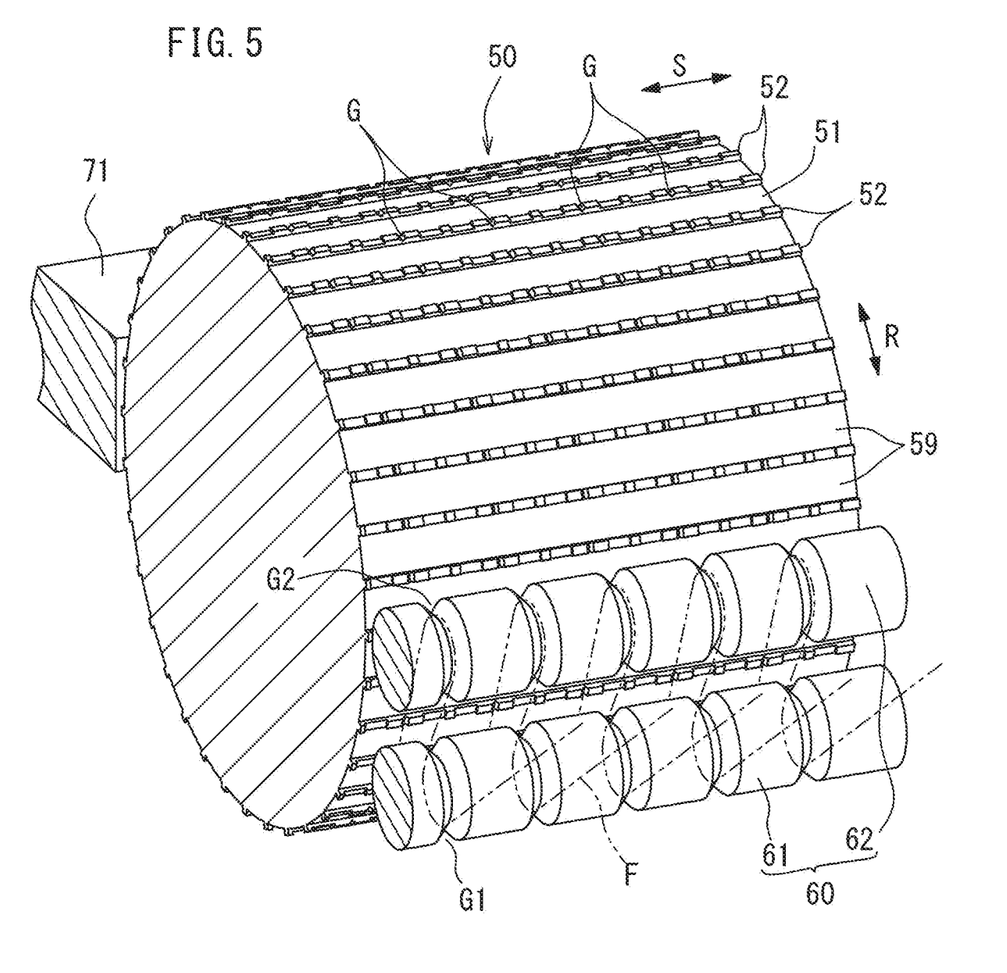
FIG. 5 is a schematic perspective view of an anvil roll viewed from the side of an introducing device.

To be more specific, the anvil roll 50 of FIG. 5 has a number of ridges (projection strips) 52 on an outer peripheral surface 51. The ridge 52 extends in the width direction S of the anvil roll 50. That is, the ridge 52 extends along a generatrix parallel to the axis direction of the anvil roll 50.

Figure 7:
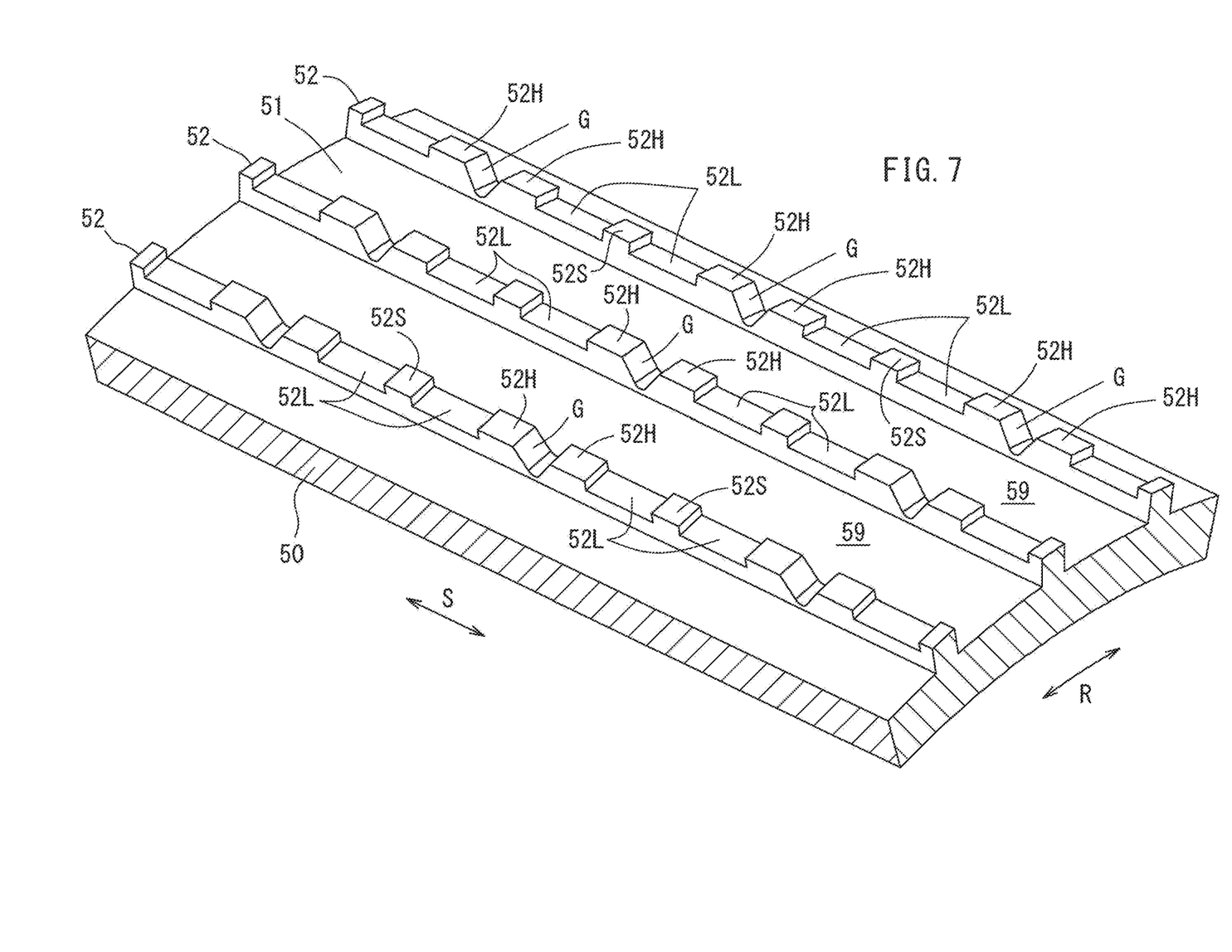
FIG. 7 is an enlarged perspective view illustrating the partially cut-out anvil roll.

In FIG. 7, the plurality of ridges 52 are spaced from each other in the circumferential direction R of the anvil roll 50, and ridges 52 adjacent to each other among the plurality of ridges 52 define a recessed groove 59 extending in the width direction S. Each of the ridges 52 has the plurality of first projections 52H provided intermittently in the width direction S, with each first projection 52H including the carrying groove G.

In this manner, with the ridges 52 and the recessed grooves 59, the first projections 52H are provided in a matrix form in the circumferential direction R and the width direction S of the roll 50, and the carrying grooves G are provided in a matrix form in the circumferential direction R and the width direction S of the roll 50.

The fusion device 70 of FIG. 4A includes a horn 71. The horn 71 is provided with ultrasonic energy, and faces the ridge 52 of FIG. 4C through the pair of sheets 1, 2 and the elastic member F.

Figure 4C:
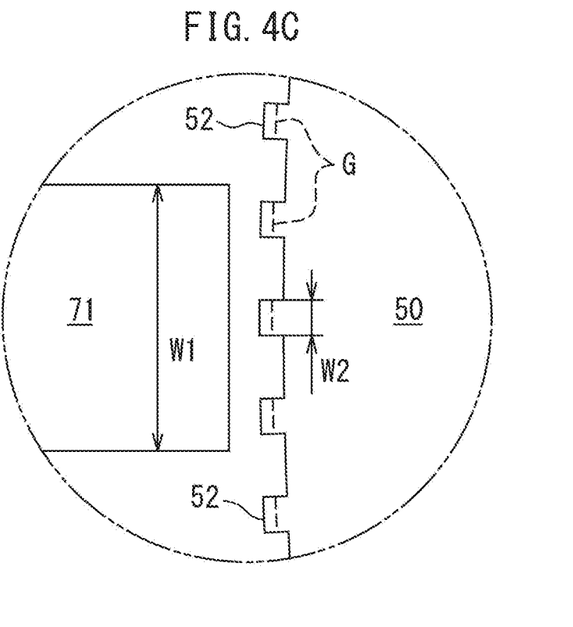
FIG. 4C is a side view of an enlarged C part.

In FIG. 4C, a width W1 of the horn 71 along the flow direction of the sheets 1, 2 may be larger than a width W2 of the ridge 52. Moreover, it is also possible to make settings such that a plurality of ridges 52 temporarily or continuously face the horn 71 at the same time.

Figure 6:
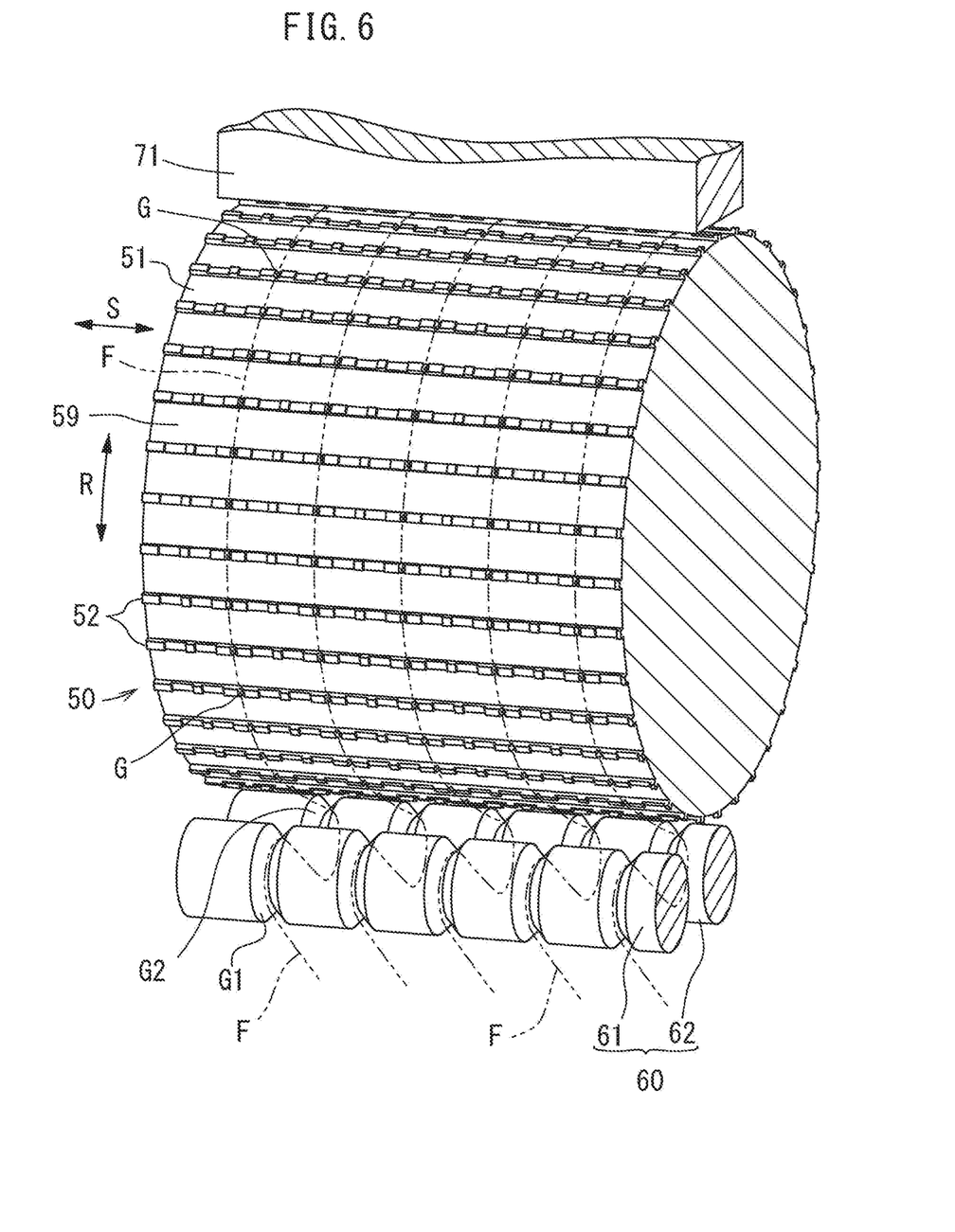
FIG. 6 is a schematic perspective view of the anvil roll viewed from the lower side.

As illustrated in FIG. 5 and FIG. 6, the anvil roll 50 has a plurality of carrying grooves G. Each of the carrying grooves G is formed by a V-shaped or U-shaped notch formed on each of the plurality of ridges 52, extends in the circumferential direction R of the anvil roll 50 to cross each of the ridges 52, and carries the elastic member F in the state where the elastic member F has entered in. The carrying groove G is recessed toward the center in the radial direction of the anvil roll 50.

Figure 9:
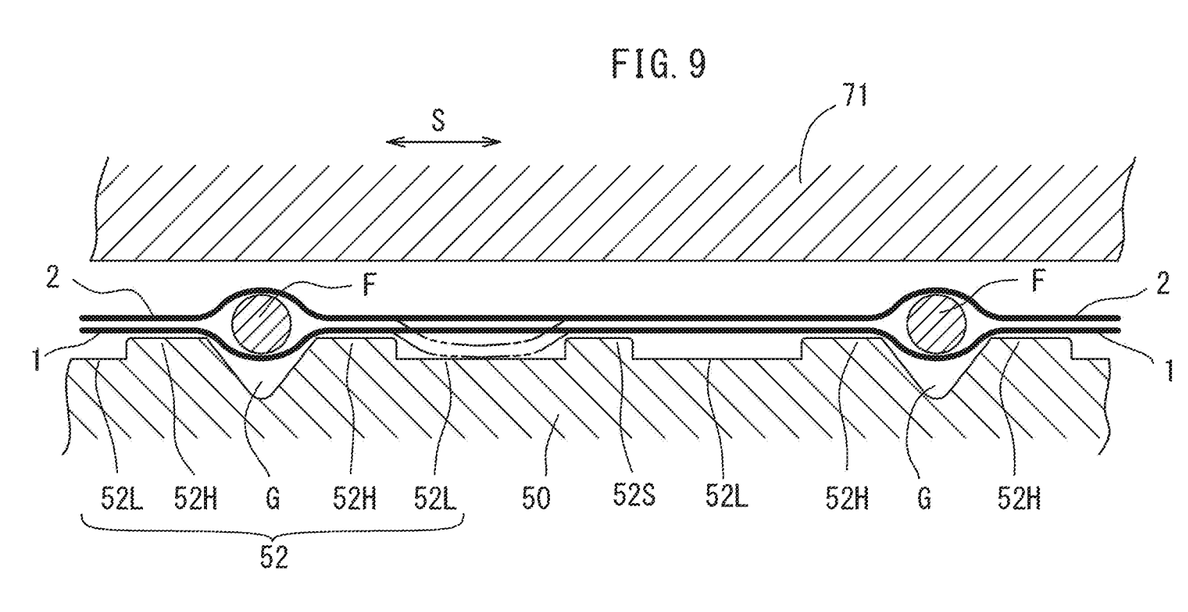
FIG. 9 is an enlarged section view of a horn and the anvil roll cut at a region of the ridges of the anvil roll.

As illustrated in FIG. 9, the size of the carrying groove G may be set so that a part of the elastic member F is housed in the groove and the remaining part is protruded from the groove. The section area of the carrying groove G may be smaller than the section area of the elastic member F of a natural length.

Note that although FIG. 5 to FIG. 8C do not illustrate the sheets 1, 2, the sheets 1, 2 are disposed to sandwich the elastic member F, as illustrated schematically in FIG. 9.

The introducing device 60 of FIG. 4A includes a first roll (regulation roll) 61 and a second roll (guide roll) 62. Each of the first and second rolls 61, 62 of FIG. 5 may have a plurality of first and second guide grooves G1, G2. Each of the elastic members F is wound on each of the first guide grooves G1 to guide each of the elastic members F. Each of the elastic members F delivered from each of the first guide grooves G1 of the first roll 61 is wound on each of the second guide grooves G2 of FIG. 6 to guide each of the elastic members F to each of the carrying grooves G of the anvil roll 50.

The first and second rolls 61, 62 may be free rollers, and may be driven to rotate in synchronization with the anvil roll 50. Moreover, the first and second rolls may not be provided.

As illustrated clearly in FIG. 7, each of the ridges 52 has the plurality of carrying grooves G, receiving parts 52L and projections 52H, 52S. That is, each of the ridges 52 includes a plurality of first projections 52H for generating the first joint portions 31, a plurality of second projections 52S for generating the second joint portions 32, and receiving parts 52L for forming the non-joint portions 33. Note that to allow easy understanding of the structure, FIG. 7, FIG. 8B, FIG. 8C, and FIG. 9 illustrate the heights of the projections 52L, 52H and the depth of the carrying groove G in an exaggerated manner.

In FIG. 7, the first and second projections 52H, 52S, and the receiving parts 52L are provided intermittently along the width direction S of the anvil roll 50, that is, while being spaced in the width direction S.

Figure 8A:
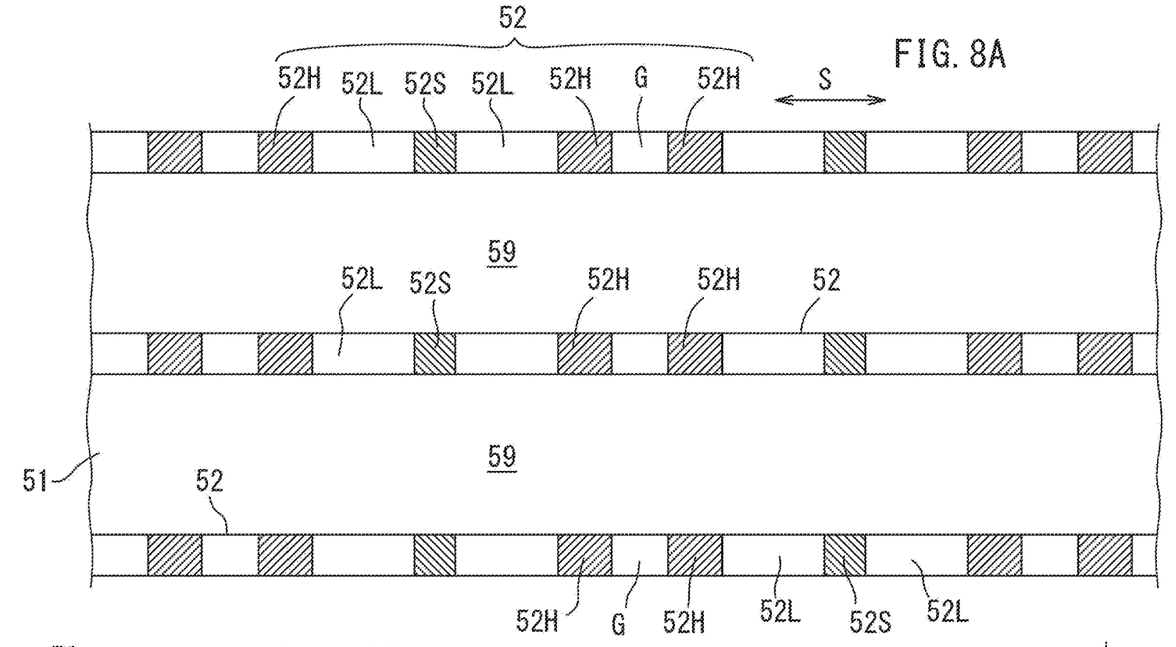
FIG. 8A, FIG. 8B, and FIG. 8C are an expanded plane view, a longitudinal section view, and a transverse section view, respectively, with ridges.
Figure 8B:
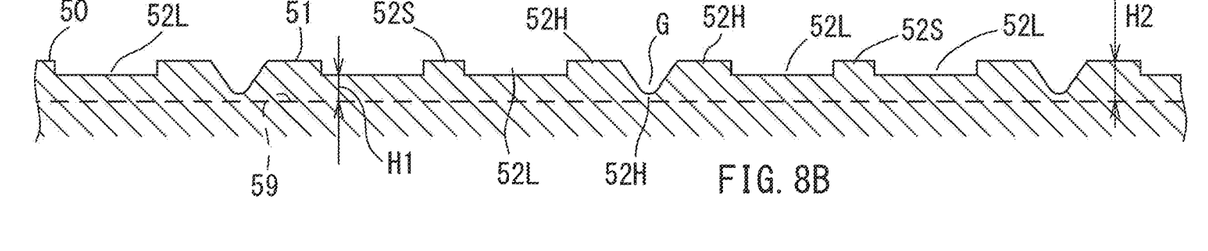
Figure 8C:
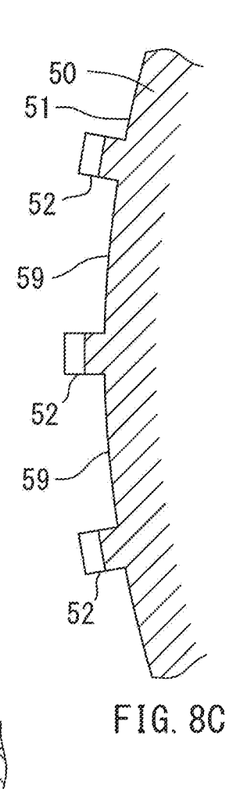

The height H1 of the receiving part 52L of FIG. 8B (height from the surface of the recessed groove 59) is smaller than the largest height H2 of the first and second projections 52H, 52S. The height H1 of the receiving part 52L is smaller by 70 to 200 μm, for example, than the height H2 of the projection 52H (height from the surface of the recessed groove 59).

In FIG. 8B, the carrying groove G is defined by the notch formed in the first projection 52H. The lowest surface of the notch of the first projection 52H is set to a height projecting in the radial direction of the roll 50 relative to the bottom surface of the recessed groove 59 illustrated by a broken line. The surface of the receiving part 52L is set to a height projecting in the radial direction relative to the lowest surface of the notch, the height retreating (lowering) in the radial direction relative to the top projection surface of the first projection 52H.

The carrying groove G is defined by (a pair of) regions on both sides in the width direction S of the first projection 52H and the region of the first projection 52H on the lower side of the carrying groove G. That is, the regions on the both sides of the first projection 52H and the region on the lower side of the same first projection 52H define the bottom surface of the carrying groove G. For example, as illustrated in FIG. 8B, a part of the first projection 52H is shaved in a V-shape form, and the carrying groove G is formed to be surrounded by the first projection 52H on the lower side and the both sides in the width direction S.

As illustrated in FIG. 7, a plurality of pairs of first projections 52H are disposed in each of the width direction S and the circumferential direction R of the anvil roll 50. Between the pair of first projections 52H and another pair of first projections 52H that are adjacent to each other in the width direction S, there is disposed the above-described at least one receiving part 52L to receive the pair of sheets 1, 2.

In the case of this example, two receiving parts 52L are provided between the pair of first projections 52H and the another pair of first projections 52H. Between the two receiving parts 52L, there is provided the second projection 52S for generating the second joint portion 32 (FIG. 2A) jointing the pair of sheets 1, 2 to each other.

The following will describe an example of the method for producing the stretchable laminate 10 using the production device.

As illustrated in FIG. 4A, the first sheet 1 is introduced to the upstream part of the anvil roll 50. A plurality of elastic members F are introduced from the introducing device 60 onto the first sheet 1 introduced to the anvil roll 50. Each of the elastic members F is introduced, in the state of having entered in the carrying groove G of FIG. 4C, together with the first sheet (FIG. 4A).

To suppress shrinkage of the first sheet 1 in the radial direction of the anvil roll 50, the first sheet 1 and the elastic member F are carried while the first sheet 1 is received at the receiving parts 52L between a pair of first projections 52H and another pair of first projections 52H as illustrated by two-dot chain lines in FIG. 9, and each pair of first projections produces (generates) the pair of first joint portions 31, 31 later.

Meanwhile, the second sheet 2 of FIG. 4A is introduced to the region of the anvil roll 50 facing the horn 71 of FIG. 4C. That is, on the anvil roll 50, the second sheet 2 is introduced onto the first sheet 1 so as to sandwich the elastic members F between the first sheet 1 and the second sheet 2.

When the first sheet 1, the elastic members F, and the second sheet 2 pass between the horn 71 and the ridges 52, the horn 71 is ultrasonically vibrated in the direction toward the anvil roll 50. In this manner, the sheets 1, 2 are fused mutually at the first joint portions 31 and the second joint portions 32 of FIG. 2A, and the sheets 1, 2 are fused to the elastic members F at the fixing parts 3*f*. Thus, the stretchable laminate 10 is generated.

Here, the first sheet 1 and the second sheet 2 are not fused at the receiving parts 52L of FIG. 7 and FIG. 8B, and the first sheet 1 and the second sheet 2 are fused on each of the projections 52H, 52S of the anvil roll 50, thus forming the joint portions 3.

As enlarged and illustrated in FIG. 9, the pair of sheets 1, 2 pass between the first projection 52H or the second projection 52S of the ridge 52 and the horn 71 in the direction orthogonal to a paper surface of the figure.

At each of the projections 52H, 52S of FIG. 9, the horn 71 is in contact with the second sheet 2 with large pressure. Therefore, each of the projections 52H, 52S intermittently generates the first and second joint portions 31, 32 of FIG. 2A in the stretching direction Df of the elastic member F, and the pair of sheets 1, 2 are ultrasonically fused securely there.

Meanwhile, in FIG. 9, at the receiving part 52L, contact pressure hardly occurs between the horn 71 and the second sheet 2. Thus, ultrasonic fusion bonding is not performed at the receiving part 52L.

Moreover, as exemplified by two-dot chain lines of FIG. 9, when the first and second sheets 1, 2 start shrinking in the radial direction of the anvil roll 50 at the receiving part 52L, the first sheet 1 is received by the surface of the receiving part 52L. Thus, it is difficult for the sheets 1, 2 to displace in the width direction S. As a result, it is possible to fuse the sheets together without protrusion of the elastic member F from the carrying groove G (without moved to an area between the projection surface of the first projection 52H and the horn 71, on which large pressure is applied), and thus without rupture of the elastic member F.

Figure 10:
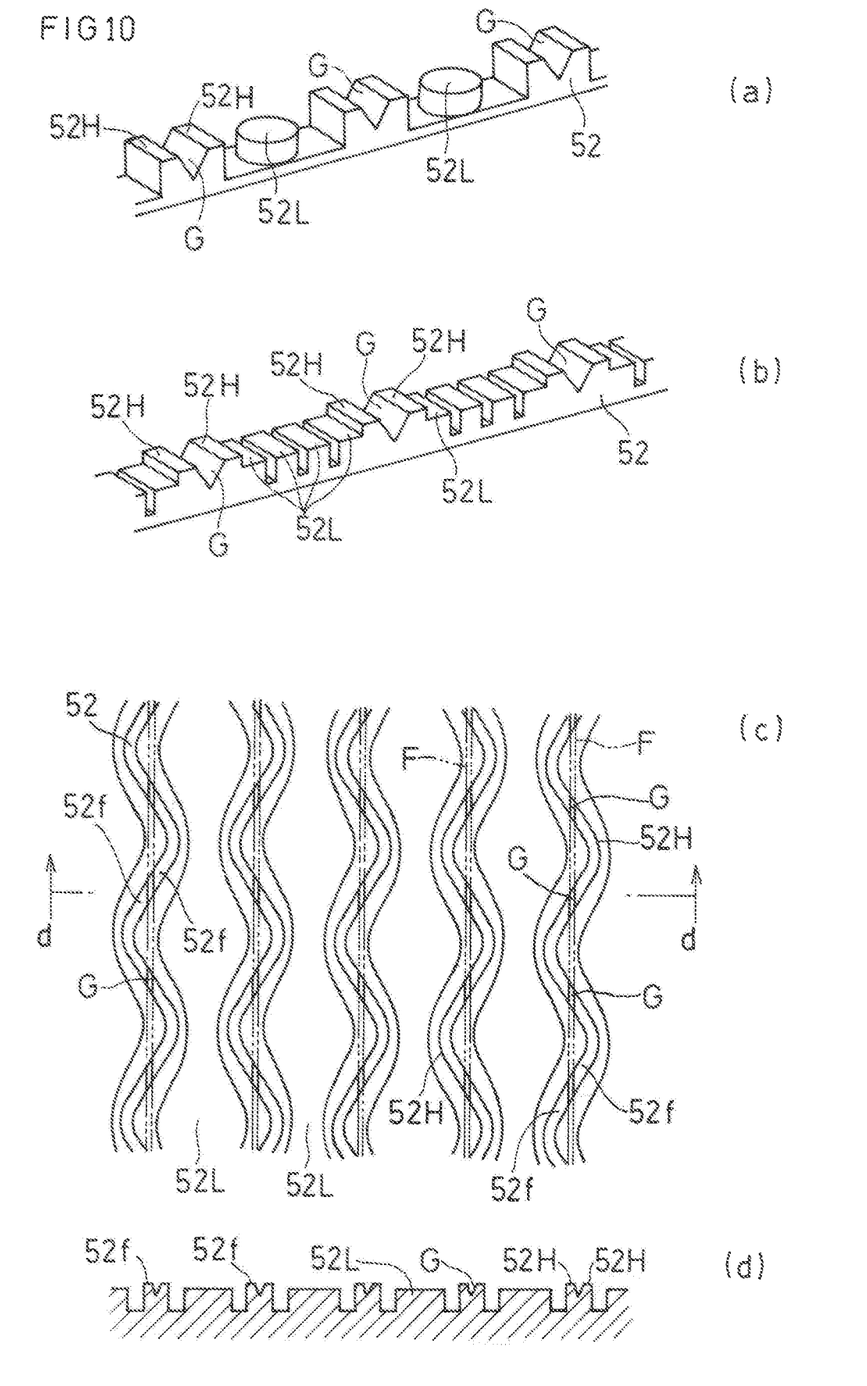
FIG. 10(a) and FIG. 10(b) are perspective views each illustrating another example of the ridges.
FIG. 10(c) is a plane view illustrating still another example of the ridges.
FIG. 10(d) is a section view cut along a d-d line of FIG. 10(c).

FIG. 10 illustrates a modification.

As illustrated in FIG. 10(a), the shape of the receiving part 52L may be circular or the like, other than rectangular. Moreover, the receiving part 52L may project further in the circumferential direction than each of the first projections 52H or may be shorter in the circumferential direction.

As illustrated in FIG. 10(b), the receiving part 52L may be continuous to the first projection 52H or may be formed intermittently.

As in the examples of FIGS. 10(c) and 10(d), the surface 52f of the ridge 52 between the first projection 52H and the receiving part 52L and the first projection 52H may meander (be continuous in a zigzag form) relative to the elastic member F of the stretchable laminate 10. In such a case, the width of the receiving part 52L may not be constant. In such a case, the carrying grooves G are provided intermittently in the first projections 52H in the extending direction of the elastic member F. That is, only at the regions where the first projection 52H crosses the elastic member F, the carrying grooves G are provided along the extending direction of the elastic member F. Note that FIG. 10(d) illustrates the elastic members F by two-dot chain lines.

Incidentally, the receiving part 52L may have the same height as the outer peripheral surface of the anvil roll 50. Moreover, although the effect; of preventing displacement of the elastic member is not expected in such a case, the receiving parts 52L may be formed at intermittent portions in the circumferential direction of the projections for jointing.

As described above, the preferred examples have been described with reference to the drawings. Upon reading the present specification, a person skilled in the art will readily arrive at various changes and modifications within an obvious range.

For example, the roll for introduction is not; necessarily provided. Moreover, the fusion bonding may not be ultrasonic but of heat sealing.

Therefore, such changes and modifications are deemed to fall within the scope of the present invention, which is defined by the appended claims.

INDUSTRIAL APPLICABILITY

The present invention may be applied to the production of the stretchable laminate that is preferably used for diaper-type and underpants-type disposable wearable articles.

REFERENCE SIGNS LIST 1, 2: Pair of sheets, 10: Stretchable laminate, 1f, 2f: First surface
3: Joint portion, 3f: Fixing part, 31: First joint portion, 32: Second joint; portion, 33: Non-joint portion.
50: Anvil roll, 51: Outer peripheral surface, 52: Ridge (projection strip), 52H: First projection, 52S: Second projection, 52L: Receiving part, 59: Recessed groove
60: Introducing device, 61: First roll (regulation roll), 62: Second roll (guide roll)
70: Fusion device, 71: Horn
Df: Stretching direction, Dp: Crossing direction, F: Elastic member
G: Carrying groove, G1: First guide groove, G2: Second guide groove
H1, H2: Height, S: Width direction (axis direction)
P: Pleat, W1 to W2: Width

The invention claimed is:

1. A device for producing a stretchable laminate for a wearable article, comprising:
   an anvil roll that carries a pair of first and second sheets and elastic members so that the elastic members are sandwiched between the pair of first and second sheets and
   a fusion device that, in cooperation with the anvil roll, fuses the pair of first and second sheets mutually and makes the pair of first and second sheets hold the elastic members, wherein
   an outer peripheral surface of the anvil roll includes a plurality of first projections for producing first joint portions with the pair of first and second sheets jointed to each other, the first projections being provided along a width direction of the anvil roll and spaced from each other in the width direction,
   each of the first projections defines and includes a carrying groove extending in a circumferential direction of the anvil roll and carrying each of the elastic members while each of the elastic members has entered in the groove, and
   at least one receiving part for receiving the pair of first and second sheets is arranged between one first projection and another first projection adjacent to each other in the width direction, among the plurality of first projections each including the carrying groove.

2. The device for producing the stretchable laminate according to claim 1, wherein
   the at least one receiving part comprises at least two receiving parts provided between the one first projection and the another first projection, and
   a second projection for producing a second joint portion with the pair of first and second sheets jointed to each other is provided between the at least two receiving parts.

3. The device for producing the stretchable laminate according to claim 1, wherein a height of the at least one receiving part is smaller than a height of the first projections by 51 to 300 μm.

4. The device for producing the stretchable laminate according to claim 1, wherein
   the outer peripheral surface of the anvil roll includes a plurality of ridges extending along the width direction of the anvil roll and spaced from each other in the circumferential direction of the anvil roll,
   those of the ridges adjacent to each other among the plurality of ridges define a recessed groove extending in the width direction,
   each of the ridges includes the plurality of first projections each having the carrying groove, the first projections being provided intermittently in the width direction, and
   the ridges and the recessed grooves are formed so that the first projections are provided in a matrix form in the circumferential direction and the width direction of the anvil roll, and the carrying grooves are provided in a matrix form in the circumferential direction and the width direction of the anvil roll.

5. A method for producing the stretchable laminate for the wearable article using the device according to claim 1, the stretchable laminate including a plurality of elastic members spaced from each other and sandwiched by a first sheet and a second sheet, the first and second sheets being jointed to each other at each of first joint portions, the first joint portions arranged in columns in a stretching direction of the elastic members and arranged in rows in a direction crossing the stretching direction, the method comprising:

a step of introducing the first sheet onto an anvil roll;

a step of introducing the elastic members onto the first sheet on the anvil roll and introducing the elastic members so that each of the elastic members enters in each of carrying grooves of the anvil roll;

a step of carrying the first sheet and the elastic members while receiving the first sheet at a receiving part between one first projection and another first projection, each including the respective carrying grooves, so as to suppress shrinkage of the first sheet in a radial direction of the anvil roll;

a step of introducing, on the anvil roll, the second sheet onto the first sheet so as to sandwich the elastic members between the first sheet and the second sheet; and a step of forming the first joint portions by fusing the first sheet and the second sheet on the one and the another first projections of the anvil roll without fusing the first sheet and the second sheet at the receiving part.

6. A method for producing the stretchable laminate for the wearable article using the device according to claim 3, the stretchable laminate including the elastic members spaced from each other and sandwiched by the pair of first and second sheets, the pair of first and second sheets being jointed to each other at each of the first joint portions, the first joint portions arranged in columns in a stretching direction of the elastic members and arranged in rows in a direction crossing the stretching direction, the method comprising:

a step of introducing the first sheet of the pair of first and second sheets onto the anvil roll;

a step of introducing the elastic members onto the first sheet on the anvil roll and introducing the elastic members so that each of the elastic members enters in each of the carrying grooves of the anvil roll;

a step of carrying the first sheet and the elastic members while receiving the first sheet at the at least one receiving part between the one first projection and the another first projection, each including the respective carrying grooves, so as to suppress shrinkage of the first sheet in a radial direction of the anvil roll;

a step of introducing, on the anvil roll, the second sheet of the pair of first and second sheets, onto the first sheet so as to sandwich the elastic members between the first sheet and the second sheet; and a step of forming the first joint portions by fusing the first sheet and the second sheet on the one and the another first projections of the anvil roll without fusing the first sheet and the second sheet at the receiving part.

7. The device for producing the stretchable laminate according to claim 2, wherein a height of the at least one receiving part is smaller than a height of the first projections by 51 to 300 μm.

* * * * *